United States Patent
Chang et al.

[11] Patent Number: 5,952,422
[45] Date of Patent: *Sep. 14, 1999

[54] POLYURETHANE PRESSURE-SENSITIVE ADHESIVES

[75] Inventors: Tak-lung Chang, Skillman; Sheng-hung Kuo, Princeton; Kishore Shah, Bridgewater; Agis Kydonieus, Kendall Park, all of N.J.

[73] Assignee: Bristol-Myers Squibb Company, New York, N.Y.

[*] Notice: This patent issued on a continued prosecution application filed under 37 CFR 1.53(d), and is subject to the twenty year patent term provisions of 35 U.S.C. 154(a)(2).

[21] Appl. No.: 08/768,735

[22] Filed: Dec. 18, 1996

Related U.S. Application Data

[63] Continuation of application No. 08/768,735, Dec. 18, 1996, abandoned.
[60] Provisional application No. 60/008,953, Dec. 20, 1995.

[51] Int. Cl.$^6$ ................ C08J 3/00; C08K 3/20; C08L 75/00; C08G 18/00
[52] U.S. Cl. .............. 524/590; 524/589; 528/44; 528/76; 528/77; 528/85; 602/54
[58] Field of Search ................... 524/589, 590; 528/44, 76, 77, 85; 602/54

[56] References Cited

U.S. PATENT DOCUMENTS

| | | | |
|---|---|---|---|
| 4,043,982 | 8/1977 | O'Sullivan et al. | 260/47 UA |
| 4,297,185 | 10/1981 | Chevreux et al. | 204/159.15 |
| 4,661,099 | 4/1987 | von Bittera et al. | 604/290 |
| 4,914,173 | 4/1990 | Ansell | 528/49 |
| 5,017,625 | 5/1991 | Ansell | 521/159 |
| 5,087,686 | 2/1992 | Ansell et al. | 528/49 |
| 5,116,930 | 5/1992 | Yabuta et al. | 528/45 |
| 5,274,045 | 12/1993 | Yukawa et al. | 525/293 |
| 5,591,820 | 1/1997 | Kydonieus et al. | 528/76 |

FOREIGN PATENT DOCUMENTS

| | | |
|---|---|---|
| 0147588 | 7/1985 | European Pat. Off. . |
| 0597636 | 5/1994 | European Pat. Off. . |
| 2199040 | 6/1988 | United Kingdom . |
| 2207867 | 2/1989 | United Kingdom . |
| 9628374 | 9/1996 | WIPO . |

OTHER PUBLICATIONS

Odian, G., Principles of Polymerization, 1981, pp. 20–25.

*Primary Examiner*—Patrick D. Niland
*Attorney, Agent, or Firm*—John M. Kilcoyne; Theodore R. Furman, Jr.

[57] ABSTRACT

Method for forming a polyurethane based adhesive composition in which a reaction mixture of at least one NCO-terminated prepolymer and a polyhydroxy compound is heated at a temperature and for a length of time sufficient to provide a gel content of from about 30 to 42% by weight and a molecular weight of extractables of at least about 45,000. Polyurethane based adhesives prepared by the method and medical devices employing the same are also disclosed.

25 Claims, No Drawings

POLYURETHANE PRESSURE-SENSITIVE ADHESIVES

This is a Continuation of application Ser. No. 08/768,735, filed Dec. 18, 1996 now abandoned, but which claims the benefit of U.S. Provisional Application No. 60/008,953, filed Dec. 20, 1995.

FIELD OF THE INVENTION

This invention relates to polyurethane pressure-sensitive adhesives. More particularly, this invention relates to polyurethane pressure-sensitive adhesives which exhibit a high degree of adhesion and a high degree of cohesive strength so as to be especially suitable for use in a medical device for application to human skin. The pressure-sensitive adhesives of the present invention are especially useful for long term use exceeding one day, typically at least five days. Another aspect of this invention relates to medical devices, including ostomy devices and wound dressings, which incorporate such polyurethane pressure-sensitive adhesives therein.

BACKGROUND OF THE INVENTION

Until the early 1950's, commonly used pressure-sensitive adhesives ("PSAs") for skin applications were based on natural or synthetic rubber compositions compounded with low molecular weight tackifiers, plasticizers, stabilizers, etc. These adhesives had the disadvantage of being hydrophobic and incapable of absorbing water. Thus, such adhesives would trap water under the covered area, often causing skin maceration or other skin damage. Furthermore, the low molecular weight ingredients compounded into these adhesives often would penetrate the skin, causing irritation or sensitization.

Polyacrylate PSAs are an improvement over the rubber-based adhesives, partly due to their self-adhesive property. This property allows them to be prepared as single-component polymeric materials without the need for potentially allergenic modifying or tackifying agents. However, these adhesives often contain unreacted residual acrylic monomer as an impurity in an amount which would irritate and/or sensitize skin. Although these polyacrylate PSAs are much more permeable to moisture or water vapor than are the rubber-based adhesives, they are incapable of absorbing any significant amounts of moisture or water. Therefore, when used for long duration in skin or wound care applications, adhesion is compromised and/or skin damage or maceration may result.

One variation of these polyacrylate PSAs is disclosed in U.S. Pat. No. 4,914,173 to Ansell. The specific PSAs of that patent are obtained by reacting an isocyanate prepolymer, which is the reaction product of a poly-functional isocyanate and a polyoxyalkylene diol monoalkyl ether, with a hydroxy-containing ester of acrylic or methacrylic acid to form a functionalized prepolymer and then cross-linking the polymer by irradiation to form a PSA that is not self-adherent but is capable of absorbing up to 95% by weight of water when hydrated. Although useful in applications where the adhesive will contact a moist or wet environment, these adhesives do not have sufficient tack or initial adhesive properties to be adherent to the skin for certain uses.

An advance in PSA formulation for skin and particularly for wound care applications was the development of compositions comprising blends of one or more water-soluble or swellable hydrocolloids and a tacky, viscous, polymeric material such as polyisobutylene as disclosed in Chen U.S. Pat. No. 3,339,546. Another example is Doyle et al. U.S. Pat. No. 4,551,490 which discloses medicinal grade pressure-sensitive compositions containing polyisobutylenes or blends of polyisobutylenes and butyl rubber, a styrenic radical or block type copolymer, mineral oil and water soluble hydrocolloid gum and a tackifier. Such hydrocolloid containing PSAs have the advantage of providing the desired adhesion to skin and, at the same time, are capable of absorbing transepidermal water loss (i.e., perspiration) or other body fluids, including wound exudates.

Hydrocolloid containing PSAs have found u se in medical applications such as ostomy devices and wound dressings, where the adhesives maintain the device on skin for several days without skin damage. However, existing hydrocolloid PSAs have certain limitations in that they are opaque, lack quick initial tack, and tend to disintegrate upon excessive water absorption. Furthermore, hydrocolloid PSAs are not flexible and/or easily conformable or repositionable on the skin. In addition, they often leave an undesirable residue on the skin.

Polyurethanes are polymeric products of diols or polyols and diisocyanates or polyisocyanates. Despite the broad applications of polyurethane chemistry, polyurethane based PSAs are not widely used and to date have been found suitable for only a few specialized applications. A suitable balance of elastic and viscous properties which is required in a PSA has not been readily attainable in conventional polyurethane materials.

Existing polyurethane based adhesives function either as weak elastomers or simply as high viscosity liquids. The adhesives composed of the elastic type polyurethanes tend to fail by gradually peeling away from surfaces to which they have been applied. The high viscosity type polyurethanes, which are typically obtained by using a substantial excess of polyol, leave a residue upon removal, and their cohesive strength is too low to withstand the stresses applied in many applications.

The difficulty of attaining this balance of viscoelastic characteristics in a polyurethane explains the limited effective use of polyurethane PSA for medical devices applied to the skin.

For example, Rolf Dahl et al., U.S. Pat. No. 3,437,622 discloses a pressure-sensitive adhesive employing a polyurethane polymer in which the isocyanate to hydroxyl group ratio is within a specified range and in which the process employs the addition of tackifiers and plasticizers. Leonard A. Tushaus, U.S. Pat. No. 3,767,040 discloses a pressure-sensitive polyurethane adhesive which has a molecular weight between crosslinks of about 6,000 to 40,000 and a urethane group concentration of about 0.7 to 1.3 per 1,000 grams of polymer. Heinz Muller et al., U.S. Pat. No. 3,930,102 discloses a self-adhesive web having a polyurethane-based adhesive thereon which is produced from a branched polyether and an aliphatic diisocyanate. Dominic Simone, U.S. Pat. No. 4,332,927 discloses the reaction of at least one NCO-terminated prepolymer and at least one polyol in the presence of a dialkyltin dicarboxylated catalyst. Dietmar Schapel, U.S. Pat. No. 4,404,296 and Hans-Heribert Burgdorfer et al., U.S. Pat. No. 4,456,642 disclose a polyol gel made from 15 to 62 weight percent of a high molecular weight covalently cross-linked polyurethane matrix and 85 to 38 weight percent of a liquid dispersing agent which is firmly bonded to the matrix. The liquid dispersing agent is a polyhydroxyl compound having a molecular weight of between 1,000 and 12,000 and an OH number between 20 and 112.

Allen et al., U.S. Pat. No. 4,497,914 discloses an ostomy gasket adhesive comprised of a polyurethane prepared by reaction of an organic polyisocyanate with one or more di or polyfunctional hydroxyl compounds.

Miklos von Bittera et al., U.S. Pat. No. 4,661,099 discloses an adhesive polyurethane gel material which is formed by immobilizing a high molecular weight polymeric polyol in a matrix of a covalently cross-linked polyurethane. Fritz Hostettler, U.S. Pat. No. 4,722,946 discloses a polyurethane formed by the reaction of a mixture of linear and branched polyols, a polyisocyanate and optionally a blowing agent at an isocyanate index of from about 65 to 85.

Francis E. Gould et al., U.S. Pat. No. 5,000,955 discloses a thermally reversible polyurethane hydrogel produced by reacting under anhydrous conditions a non-aromatic organic diisocyanate, with a glycol component in an NCO/OH mole weight ratio of from about 0.900 to 0.980:1. Robert B. Orr, U.S. Pat. No. 5,157,101 discloses a pressure-sensitive polyurethane based adhesive including an isocyanate reactant and an active hydrogen reactant. Dietmar Schapel et al., U.S. Pat. No. 5,362,834 discloses gel compounds based on reaction products of polyols and polyisocyanates in which different polyol components are used, one being one or more polyols having a hydroxyl value below 112 and the other being one or more polyols having hydroxyl values of from 112 to 600.

Despite these efforts, commercially acceptable pressure-sensitive polyurethane adhesives for use particularly with medical devices which attach to the patients' skin such as wound dressings and ostomy appliances have not been successful. While polyurethane based adhesives generally are less irritating to the skin than acrylic based adhesives and have better strength, polyurethane based adhesives remain problematical. This is because it has heretofore been difficult to provide a polyurethane based adhesive which exhibits excellent adhesion over an extended period of time (e.g. 5 days) while maintaining a high degree of cohesive strength so that the medical device can withstand the riggers of 5 day wear.

It would therefore be a significant advance in the art of medical devices applied to the skin to provide an adhesive composition which exhibits excellent adhesion and excellent cohesive strength over extended periods of wear without irritating the patients' skin.

SUMMARY OF THE INVENTION

The present invention is generally directed to polyurethane-based adhesive compositions and methods of making the same in which the composition exhibits both excellent adhesive properties and cohesive strength. The present invention also encompasses medical devices such as wound dressings and ostomy appliances which incorporate the polyurethane composition and to methods of making such devices.

The present invention is premised on the discovery that there is a relationship between the gel content of the polyurethane adhesive and the molecular weight of the extractables contained within the composition which, when controlled in well-defined ranges, results in a superior adhesive composition exhibiting both excellent adhesion and cohesive strength.

More specifically the present invention is directed to a polyurethane-based adhesive and method of making the same and to medical devices employing the same. In particular, the present invention is directed to a method of forming a polyurethane-based adhesive composition comprising:

(a) reacting at least one NCO-terminated prepolymer with a polyhydroxyl compound to form a reaction mixture; and (b) heating the reaction mixture at a temperature and for a length of time sufficient to provide a gel content of the adhesive composition in the range of from about 30 to 42 percent by weight and a molecular weight of extractables of at least about 45,000.

Polyurethane based adhesives having a gel content of from 30 to 42 percent by weight and extractables having a molecular weight of at least about 45,000 results in an adhesive composition which can adhere to a patients' skin without irritation for 5 days or more and which exhibits excellent cohesive strength.

DETAILED DESCRIPTION OF THE INVENTION

The present invention is directed to polyurethane pressure-sensitive adhesives, methods of making the same and medical articles such as wound dressings and ostomy appliances employing the same. The polyurethane pressure-sensitive adhesive composition is prepared by first reacting at least one NCO-terminated prepolymer with a polyhydroxyl compound to form a reaction mixture. The reaction mixture is then formed into a sheet and heated at a temperature and for a length of time (e.g. residence time) sufficient to provide a gel content of from about 30 to 42 percent by weight and having extractables contained within the composition characterized by a molecular weight of at least 45,000.

As used herein the term "gel content" means the percent by weight of the components of the pressure sensitive adhesive composition which are formed by crosslinking of the prepolymer and the polyhydroxyl compound. The gel portion is what provides cohesive strength to the adhesive composition.

The term "extractables" is synonymous with the soluble portion of the adhesive composition. The soluble components contribute to the adhesive tack. The combination of gel and soluble components determine the adhesive properties. Generally, the molecular weight of the extractables comprising the soluble portion of the adhesive composition is critical to the attainment of aggressive adhesive characteristics required for long term wear on human skin. If the molecular weight of the extractables is too low then a residue will be left on the skin. In addition, exceptionally high molecular weight values for the extractables generally results in an adhesive which adheres too strongly to the skin and can thereby cause patient discomfort when the medical appliance is removed.

The first step of the reaction process is the reaction of at least one NCO-terminated prepolymer with a polyhydroxy compound. The NCO-terminated prepolymer may be made by reacting a polyhydroxyl compound with an isocyanate. The preferred polyhydroxyl compounds are polyols having a molecular weight of from about 1,000 to about 10,000. Although any of a wide variety of polyols can be used, those which are not crystalline are preferred. Exemplary polyols include polyetherdiols or triols (ethylene oxide and propylene oxide polymers and copolymers) such as those available from Olin (e.g. Poly G series).

Where increased moisture or water absorption properties are desired in the pressure-sensitive adhesive, polyols that contain a significant amount of polyoxyethylene are used to increase the hydrophilic character of the polymer. These polyols should contain at least about 30 percent of polyoxyethylene in order to enable the polymer to absorb water in an amount of at least 20 percent of its weight and as high as 400 to 1,000 percent. Typical polyols which are useful for this embodiment include DOW Chemicals XUS 15176 and the various commercial Carbowaxes which are available in a range of molecular weights from the Union Carbide Corporation. Representative Carbowaxes are PEG (Carbowax 1450) and PEG (Carbowax 8000) in which the numbers refer to molecular weights.

The functionality of the polyol that is used is at least 2 and usually is greater than 2, with the higher functionalities providing increased crosslinking of the polyurethane. It will be understood, however, that the functionality of the polyol and the extent of the crosslinking is governed by the requirement that the gel content of the pressure sensitive adhesive be in the range of from about 30 to 42 percent.

The isocyanates which may be used in the making of the NCO-terminated prepolymer may be represented by R(NCO)n where n is at least 2 and preferably between about 2 and 4, and R is an aliphatic, alicyclic, aliphatic-alicyclic, aromatic or aliphatic-aromatic hydrocarbon compound having from about 4 to 26 carbon atoms, preferably from about 6 to 20 carbon atoms and more preferably from about 6 to 13 carbon atoms.

Suitable polyols are set forth in Table 1.

TABLE 1

SUITABLE POLYOLS

| COMPONENT: | | FUNCTIONALITY | EQUIVALENT | ETO % | SUPPLIER |
|---|---|---|---|---|---|
| POLY G | 26-37 | 2 | 1512.00 | 0 | OLIN |
|  | 55-28 | 2 | 2025.00 | 30 | OLIN |
|  | 55-37 | 2 | 1512.00 | 30 | OLIN |
|  | 55-56 | 2 | 976.00 | 45 | OLIN |
|  | 76-120 | 3 | 457.00 | 30 | OLIN |
|  | 83-34 | 3 | 1576.00 | 70 | OLIN |
|  | 85-28 | 3 | 2025.00 | 10 | OLIN |
|  | 85-36 | 3 | 1508.00 | 17 | OLIN |
| VORANOL | 5148 | 3 | 2357.00 | 19 | DOW |
|  | 5287 | 2 | 1018.00 | 12 | DOW |
|  | 5471 | 3 | 1603.00 | 14 | DOW |
| VORAN | 220-037 | 2 | 1500.00 | 0 | DOW |
|  | 232-034 | 3 | 1636.00 | 14 | DOW |
|  | 240-446 | 4.5 | 125.10 | 0 | DOW |
|  | 240-800 | 4 | 69.70 | 0 | DOW |
|  | 270-370 | 7 | 155.90 | 0 | DOW |
| XUS | 15176.00 | 2 | 1500.00 | 30 | DOW |
| MULTRANOL | 3400 | 3 | 1000.00 | 0 | BAYER |
| MULTRANOL | 3901 | 3 | 1997.00 | 0 | BAYER |
| MULTRANOL | 9133 | 3 | 53.95 | 0 | BAYER |
| DESMOFEN | 2500 | 2 | 505.00 | 0 | BAYER |
| QUADROL |  | 4 | 73.00 | 0 | BAYER |
| CARBOWAX | 1450 | 2 | 714.00 | 100 | CARBIDE |
|  | 3350 | 2 | 1638.00 | 100 | CARBIDE |
|  | 4600 | 2 | 2352.00 | 100 | CARBIDE |
|  | 8000 | 2 | 4141.00 | 100 | CARBIDE |
| TERATHANE | 1000 | 2 | 500 | 0 | DUPONT |
|  | 2000 | 2 | 1024.00 | 0 | DUPONT |
| PLURACOL | 380 | 3 | 2235.00 | 0 | BASF |
| POLY THF ER | 1250 | 2 | 625 | 0 | BASF |
| FOMREZ | EPD-56 | 2 | 1041.00 | 45 | WITCO |
|  | EPD-28 | 2 | 2086.00 | 45 | WITCO |
|  | K22-170 | 6 | 308.00 | 90 | WITCO |
|  | L49-28 | 3 | 1990.00 | 25 | WITCO |
|  | ECFL10007 | 3 | 278.00 | 90 | WITCO |
| WITCONL | PEG1000L | 2 | 505.00 | 90 | WITCO |

Representative examples of diisocyanates include aliphatic isocyanates such as tetramethylene diisocyanate; hexamethylene diisocyanate; trimethylhexamethylene diisocyanate; dimer acid diisocyanate; isophorone diisocyanate; diethylbenzene diisocyanate; decamethylene 1,10-diisocyanate; cyclohexylene 1,2-diisocyanate and cyclohexylene-1,4-diisocyanate and the aromatic isocyanates such as 2,4- and 2,6-tolylene diisocyanate; 4,4-diphenylmethane diisocyanate; 1,4-naphthalene diisocyanate; dianisidine diisocyanate; toluidine diisocyanate; m-xylylene diisocyanate; tetrahydronaphthalene-1,5-diisocyanate; and bis (4-isocyanatophenyl)methane.

Polymeric polyisocyanates having a functionality of greater than 2, such as neopentyl tetraisocyanate, can also be used. A number of suitable commercial isocyanates are listed in Table 2 below.

TABLE 2

SUITABLE ISOCYANATES

| COMPONENT: | FUNCTION-ALITY | EQUIVALENT | SUPPLIER |
|---|---|---|---|
| PAPI 94 | 2.2 | 131.50 | DOW |
| PAPI 2580 | 3 | 139.60 | DOW |
| ISONATE 2181 | 2 | 182.60 | DOW |
| ISONATE 2125M | 2 | 125.50 | DOW |
| MONDUR MR | 2.7 | 131.00 | BAYER |
| MONDUR CD | 2 | 143.00 | BAYER |
| MONDUR CB75 | 3 | 323.00 | BAYER |
| DESMODUR W | 2 | 132.00 | BAYER |
| TMXDI | 2 | 122.10 | CYANAMID |
| CYTHANE 3160 | 3 | 404.00 | CYANAMID |
| TDI 80 | 2 | 87.00 | OLIN |
| DMI 1410 | 2 | 295.77 | HENKEL |
| DESMODUR N-3300 | 3.5 | 194.00 | BAYER |

In addition, mixtures of di- and tri-functional isocyanates are commercially available and may be used to obtain isocyanate components having a functionality of between 2 and 3, while mixtures of tri- and tetra-functional isocyanates may be used to obtain functionalities of between 3 and 4 (i.e., DESMODUR N-3300 from Bayer, Perkasie, Pa.). Desmodur N 3300 has a functionality of about 3.4–3.6 and it is a mixture of the two isocyanates depicted above. This isocyanate compound is preferred from the standpoint of toxicity because it is an aliphatic isocyanate derivative that produces a non-toxic degradation product. Furthermore, the isocyanate compounds shown above can be mixed together or with the diisocyanates mentioned above to attain the desired functionality of the isocyanate component.

Generally speaking, the polyurethane is prepared from about 75% to 95% of the polyol, and about 5% to 25% of the polyisocyanate. The relative amounts are selected so that the NCO/OH ratio is between about 0.5 and 0.99:1 and preferably between about 0.65 to 0.9:1, so that these polyurethanes have excess hydroxyl functionality.

In preparing the polyether polyurethane adhesives of this invention, the polyols and the polyisocyanates are reacted in the presence of known catalysts for such reaction, for example, tin salts and organic tin esters such as dibutyltin dilaurate and stannous octoate. An advantageous catalyst is METACURE T-12 by Air Products and Chemicals, Inc., and another is C1707 by CasChem, Inc. These catalysts have been approved by the FDA for medical applications and provide a satisfactory reaction.

The adhesive is prepared by first casting a mixture of the isocyanates, polyols, and catalyst onto the desired substrate and curing it by heating in the desired temperature range and residence time to obtain a gel content of from about 30 to 42 percent by weight and a molecular weight of extractables of $\geq 45,000$.

Alternatively, process of the present invention may begin with an NCO-terminated prepolymer which can be produced by the controlled reaction of a polyol (e.g. POLY G-26-37 made by Olin) and a polyisocyanate (e.g. DESMODUR N-3300) in the presence of a catalyst such as dibutyltin dilaurate. Preferred NCO-terminated prepolymers have a molecular weight of from about 12,000 to 29,000.

The NCO-terminated prepolymer is reacted with the polyhydroxyl compound under heating. In accordance with the present invention, the temperature of the reaction as well as the residence time of the reactants are important factors in controlling the gel content of the adhesive and the molecular weight of the extractables.

The gel content can be measured in accordance with the following procedure. Strips of the material to be tested are weighed and placed in a vessel. A solvent such as acetonitrile is added to the vessel and the vessel is capped. The vessels are gently heated under stirring to about 50° C. The sample strips are removed and placed into a second vessel and allowed to cool. The gel content is based on the weight loss of the strips in the second vessel and the extract recovered from the first vessel.

The molecular weight of the extractables can be measured in the following manner.

A vessel containing a known weight of a polyurethane adhesive prepared in accordance with the present invention is dissolved in a suitable solvent such a tetrahydrofuran. The vessel is shaken, typically for at least three hours, a suitable quantity of solution is removed from the vessel using a syringe. The solution is then filtered such as for example a 0.5 $\mu$m filter into a vial used in gel permeation chromatography.

The vial is subjected to gel permeation chromatography using, for example, styragel $HR_1$, $HR_2$ and $HR_4$ at a suitable flow rate, e.g. 1.0 ml/min of tetrahydrofuran. A standard curve is prepared using polystyrene standards having a fixed molecular weight such as between 70,000 and 78,000. The resulting chromatograms are measured and the molecular weight of the extractables determined.

The procedure may also include having at least one control run using a polyurethane adhesive composition having a known molecular weight of extractables.

In general, the higher the temperature the lower the gel content. While a wide range of temperatures may be employed to provide the desired gel content, typical temperatures are selected within the range of from about 100 to 170° C. For example, for a reactive system containing DESMODUR W, DESMODUR N-3300, POLY G 26-37 and CasChem 1707 it has been determined that typically a temperature of from about 140 to 165° C., most typically from about 145 to 165° C. will provide the desired gel content. Also, it has been observed that the residence time of the curing process impacts on the gel content and molecular weight of the extractables. The reaction is typically conducted for at least 0.5 minutes. It is preferred that the residence time be in the range from about 0.5 to 3.0 minutes, most preferably from about 1.0 to 2.0 minutes for adhesives which are from about 4 to 8 mils thick. For even thicker adhesives, the residence time should be correspondingly increased.

The relationship between gel content (GC) and molecular weight of the extractables (Emw) is shown by the Adhesivity Index (AI) which is defined in accordance with the following equation:

$$AI = \frac{Emw}{GC} \times .001$$

The preferred Adhesivity Index for adhesives in accordance with the present invention is $\geq 1.5$, more preferably from about 1.6 to 2.8, most preferably from about 1.7 to 2.4.

EXAMPLE I

An NCO-terminated prepolymer mixture (I) was prepared by charging 74.33 parts of POLY G 26-37 polyol, 3.80 parts of DESMODUR N-3300, 15.20 parts of DESMODUR W and 0.49 parts of dioctyl tin diricinoleate (CasChem Inc. C-1707) catalyst into a dry three-neck round bottom flask. The reaction mixture was then heated at 90° C. for about one hour with stirring and under a blanket of dry nitrogen gas. After the reaction was completed, the reaction mixture was allowed to cool to room temperature. To this viscous prepolymer, another 6.18 parts of DESMODUR N-3300 were added with stirring to obtain a homogenous NCO-terminated prepolymer mixture.

A polyurethane adhesive/non-woven fabric tape was prepared by first vigorously mixing 35.1 parts of the NCO-terminated prepolymer mixture (I) and 64.9 parts of POLY G 26-37(polyG 26-37/NCO-prepolymer ratio R=1.85) at room temperature for about 20 minutes. The reaction mass was then cast onto a support release paper to a thickness of about 6 mils and cured at 160 C. for 1.5 minutes. The adhesive was laminated to a polyester non-woven backing and post-cured in an air circulating oven at 90° C. for 90 minutes. A clear pressure-sensitive adhesive tape was then tested for gel content and molecular weight of extractables as described previously.

Adhesive tapes with different gel content numbers were prepared by the same procedure except that different curing conditions were used. Table 1 shows the effect of curing condition on the gel content numbers of the adhesive tapes. Adhesive with 45% gel content prepared from curing at 120 C. was found to be only good for one day wear but not adequate for 5 day wear. On the other hand the sample with 38% gel content processed at 160 C. was found good for up to 5 day wear. The results are shown in Table I.

TABLE I

| Curing Condition | | |
|---|---|---|
| Temperature (C.) | Residence Time (Min) | Gel Content (%) |
| 120 | 3 | 45 |
| 140 | 3 | 43 |
| 160 | 1.5 | 38 |

EXAMPLE II

Adhesive samples with low molecular weight of acetonitrile extractables were evaluated for its relationship with gel content and adhesive performance.

Adhesives were prepared using the same method as Example I except that a higher molecular weight (Mw=30,000) of NCO-terminated prepolymer mixture(II) was used. High molecular weight NCO-terminated prepolymer (II) was prepared by aging the regular NCO-terminated prepolymer (I) at 60 C. oven for 7 days to increase the molecular weight average (Mw) of the prepolymer from 17,000 to 30,000. The results are shown in Table II.

TABLE II

| Curing Temp. (C.) | Condition Residence Time(min) | Ratio (R) | Gel Content (%) | Molecular Weight | Activity Index* |
|---|---|---|---|---|---|
| 160 | 1.0 | 2.05 | 44.1 | 37200 | 0.84 |
| 160 | 1.0 | 2.24 | 36.4 | 38300 | 1.05 |
| 160 | 1.25 | 2.34 | 33.6 | 44300 | 1.32 |

*Adhesivity Index = (Molecular weight/Gel Content) × 0.001

Clinical evaluation showed that as the Adhesivity Index increased the adhesion to skin improved. However even at the low gel content of 33.6% the adhesivity was not adequate.

EXAMPLE III

Adhesives were prepared using the same method shown in Example I except that the Poly G26-37 to prepolymer ratio was 1.90. The results are shown in Table III.

TABLE III

| Curing Temp. (C.) | Condition Residence Time(min) | Gel Content (%) | Molecular Weight (Mw) | Adhesivity Index |
|---|---|---|---|---|
| 140 | 2.0 | 29.0 | 61000 | 2.10 |
| 150 | 2.0 | 27.0 | 68300 | 2.53 |
| 160 | 1.5 | 25.1 | 70200 | 2.80 |

Clinical results showed that adhesives having low gel content and high molecular weight of extractables are good for more than 5 day wear. However there was slight residue left on the skin.

EXAMPLE IV

Additional examples were prepared in accordance with the method of Example I having the gel content and molecular weight of extractables as shown in Table IV.

TABLE IV

| Test Product | Gel % | MW of Acetonitrile Extractables | Peel at 24 hr N/cm | Adhesivity Index | Adherence* % |
|---|---|---|---|---|---|
| A | 40.1 | 55770 | 0.40 | 1.40 | 62 |
| B | 36.3 | 61991 | 0.60 | 1.71 | 95 |
| C | 36.5 | 63251 | 0.56 | 1.73 | 95 |
| D | 42.0 | 83339 | 0.81 | 1.98 | 91 |

*Firmly adhered or slightly edge lifted

As shown in Table IV, adhesive compositions having an Adhesivity Index greater than 1.5 exhibited excellent adherence to the skin and exceptional cohesive strength.

What is claimed:

1. A method of forming a polyurethane based adhesive composition comprising:
   (a) reacting at least one NCO-terminated prepolymer with a polyhydroxy compound to form a reaction mixture; and (b) heating the reaction mixture at a temperature and for a length of time sufficient to provide a gel content in the range of from about 30 to 42 percent by weight and a molecular weight of extractables at least about 45,000.

2. The method of claim 1 wherein the polyhydroxy compound is propylene oxide polyol.

3. The method of claim 1 wherein the gel content and molecular weight of extractables satisfy the following relationship:

$$\frac{\text{molecular weight of extractables}}{\text{Gel Content}} \times .001 \geq 1.5.$$

4. The method of claim 3 wherein the gel content and molecular weight of extractables satisfy the following relationship:

$$\frac{\text{molecular weight of extractables}}{\text{Gel Content}} \times .001 = 1.6 \text{ to } 2.8.$$

5. The method of claim 1 wherein the NCO-terminated prepolymer is prepared by reacting a polyhydroxy compound with an isocyanate compound.

6. The method of claim 5 wherein the polyhydroxy compound used to prepare the NCO-terminated prepolymer is propylene oxide polyol.

7. The method of claim 5 comprising reacting the isocyanate compound with a polyether diol of a hydroxyl terminated poly(oxyalkylene) polyol.

8. The method of claim 1 comprising reacting the NCO-terminated prepolymer with the polyhydroxy compound at a molar ratio of from about 0.5 to 0.99:1.

9. The method of claim 8 wherein the molar ratio is from about 0.65 to 0.90:1.

10. The method of claim 1 wherein the NCO-terminated prepolymer has a molecular weight of from about 12,000 to 29,000.

11. The polyurethane based adhesive produced by the process of claim 1.

12. A polyurethane based adhesive having a gel content in the range of from about 30 to 42 percent by weight and a molecular weight of extractables of at least about 45,000.

13. A method of forming a polyurethane adhesive composition containing medical device for application to the skin of a patient comprising:

(a) reacting at least one NCO-terminated prepolymer with a polyhydroxy compound to form a reaction mixture;

(b) heating the reaction mixture at a temperature and for a length of time sufficient to provide a gel content in the range of from about 30 to 42 percent by weight and a molecular weight of extractables at least about 45,000 to form said adhesive; and (c) applying said adhesive composition to a surface of the medical device which contacts the patients' skin.

14. The method of claim 13 wherein the polyhydroxy compound is propylene oxide polyol.

15. The method of claim 13 wherein the gel content and molecular weight of extractables satisfy the following relationship:

$$\frac{\text{molecular weight of extractables}}{\text{Gel Content}} \times .001 \geq 1.5.$$

16. The method of claim 15 wherein the gel content and molecular weight of extractables satisfy the following relationship:

$$\frac{\text{molecular weight of extractables}}{\text{Gel Content}} \times .001 = 1.6 \text{ to } 2.8.$$

17. The method of claim 13 wherein the NCO-terminated prepolymer is prepared by reacting a polyhydroxy compound with an isocyanate compound.

18. The method of claim 17 wherein the polyhydroxy compound used to prepare the NCO-terminated prepolymer is propylene oxide polyol.

19. The method of claim 17 comprising reacting the isocyanate compound with a polyether diol of a hydroxyl terminated poly(oxyalkylene) polyol.

20. The method of claim 13 comprising reacting the NCO-terminated prepolymer with the polyhydroxy compound at a molar ratio of from about 0.5 to 0.99:1.

21. The method of claim 20 wherein the molar ratio is from about 0.65 to 0.90:1.

22. The method of claim 13 wherein the NCO-terminated prepolymer has a molecular weight of from about 12,000 to 29,000.

23. The medical device produced by the process of claim 13.

24. A medical device for application to the skin of a patient comprising a skin contacting surface having thereon a polyurethane based adhesive composition having a gel content in the range of from about 30 to 42 percent by weight and a molecular weight of extractables of at least about 45,000.

25. The medical device of claim 24 wherein the gel content and molecular weight of extractables satisfy the following relationship:

$$\frac{\text{molecular weight of extractables}}{\text{Gel Content}} \times .001 \geq 1.5.$$

* * * * *